(12) United States Patent
Wang et al.

(10) Patent No.: US 11,472,775 B2
(45) Date of Patent: Oct. 18, 2022

(54) HALOGEN-SUBSTITUTED COMPOUND, PREPARATION METHOD THEREFOR, AND USE THEREOF

(71) Applicant: Suqian Keylab Biochemical Co., Ltd., Suqian (CN)

(72) Inventors: Mingchun Wang, Suqian (CN); Qingyi Li, Suqian (CN)

(73) Assignee: Suqian Keylab Biochemical Co., Ltd., Suqian (CN)

( * ) Notice: Subject to any disclaimer, the term of this patent is extended or adjusted under 35 U.S.C. 154(b) by 0 days.

(21) Appl. No.: 17/429,640

(22) PCT Filed: Dec. 20, 2019

(86) PCT No.: PCT/CN2019/126839
§ 371 (c)(1),
(2) Date: Aug. 10, 2021

(87) PCT Pub. No.: WO2021/022761
PCT Pub. Date: Feb. 11, 2021

(65) Prior Publication Data
US 2022/0089546 A1 Mar. 24, 2022

(30) Foreign Application Priority Data
Aug. 2, 2019 (CN) .......................... 201910709834.2

(51) Int. Cl.
C07D 231/14 (2006.01)
C07D 295/14 (2006.01)

(52) U.S. Cl.
CPC ......... *C07D 231/14* (2013.01); *C07D 295/14* (2013.01)

(58) Field of Classification Search
CPC ........................... C07D 231/14; C07D 295/14
See application file for complete search history.

(56) References Cited

FOREIGN PATENT DOCUMENTS

| | | |
|---|---|---|
| CN | 107663172 A | 2/2018 |
| CN | 107987021 A | 5/2018 |
| CN | 110577503 A | 12/2019 |
| EP | 2008996 A1 | 12/2008 |
| WO | 9212970 A1 | 8/1992 |
| WO | 03051820 A1 | 6/2003 |
| WO | 2009000442 A2 | 12/2008 |
| WO | 2009043444 A1 | 4/2009 |
| WO | 2009133178 A1 | 11/2009 |
| WO | 2012025469 A1 | 3/2012 |

*Primary Examiner* — Shawquia Jackson
(74) *Attorney, Agent, or Firm* — Bayramoglu Law Offices LLC

(57) ABSTRACT

A preparation method for a halogen-substituted compound is provided, where a piperazine derivative shown in formula I reacts with a halogenated acetyl halide derivative shown in formula VI to generate a halogen-substituted compound shown in formula II. The present invention further relates to a preparation method for preparing a pyrazole derivative by using a halogen-substituted compound, where a halogen-substituted compound shown in formula II reacts with methylhydrazine to close a pyrazole ring, to generate a halogen-substituted alkyl-1-methylpyrazole derivative shown in formula IV, or reacts with methylhydrazine benzaldehyde hydrazone to generate a hydrazone compound shown in formula III, which closes, under the action of an acid, a pyrazole ring to generate a halogen-substituted alkyl-1-methylpyrazole derivative shown in formula IV. The present invention further relates to a structure of an intermediate compound. The preparation methods for a halogen-substituted compound and a pyrazole derivative are suitable for industrial production.

8 Claims, 2 Drawing Sheets

HALOGEN-SUBSTITUTED COMPOUND, PREPARATION METHOD THEREFOR, AND USE THEREOF

CROSS REFERENCE TO THE RELATED APPLICATIONS

This application is the national phase entry of International Application No. PCT/CN2019/126839, filed on Dec. 20, 2019, which is based upon and claims priority to Chinese Patent Application No. 201910709834.2, filed on Aug. 2, 2019, the entire contents of which are incorporated herein by reference.

TECHNICAL FIELD

The present invention relates to an industrial synthesis method for a halogen-substituted compound, and belongs to the field of chemical synthesis technologies.

BACKGROUND

Halogen-substituted pyrazole derivatives, particularly, fluorine-containing pyrazole derivatives, are intermediates for many medicines or pesticides. Among the fluorine-containing pyrazole derivatives, 3-difluoromethyl-1-methylpyrazole-4-carboxylic acid is an important pesticide intermediate, and plays a very important role as an intermediate in many new varieties of pesticides, for example, Bayer CropScience's cereal fungicide Bixafen, BASF's new fungicide Fluxapyroxad, Syngenta's Isopyrazam and Sedaxane, and the like.

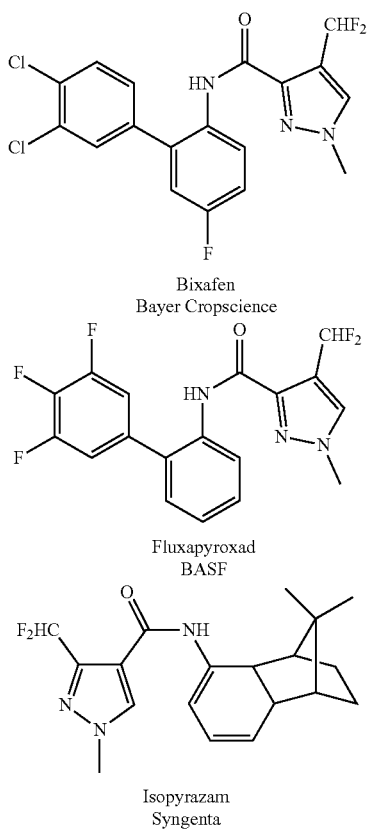

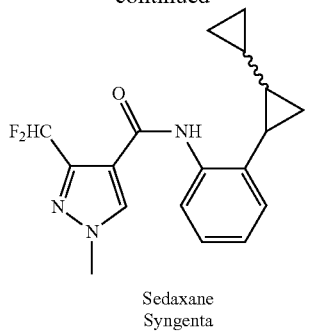

The international patent WO1992/12970 discloses 3-(difluoromethyl)-1-methyl-1H-pyrazole-4-carboxylic acid and use thereof as a fungicide. In this method, 3-(difluoromethyl)-1-methyl-1H-pyrazole-4-carboxylic acid is converted into corresponding acid chloride, and then, is converted into corresponding amide by using an appropriate amine, so as to prepare an amide fungicide.

Because 3-(difluoromethyl)-1-methyl-1H-pyrazole-4-carboxylic acid is a key intermediate for synthesizing the foregoing new amide fungicides, researches on the synthesis processes thereof stimulate extensive researches by chemists. The existing preparation methods can be concluded into the following categories:

I. Claisen condensation method, mainly reported by patents of BASF and Syngenta: This method starts from ethyl difluoroacetate, which undergoes a Claisen condensation reaction, to obtain ethyl difluoroacetoacetate, then the ethyl difluoroacetoacetate is condensed with triethyl orthoformate to obtain 4,4-difluoro-2-(ethoxymethylene)-3-oxobutyric acid ethyl ester, the 4,4-difluoro-2-(ethoxymethylene)-3-oxobutyric acid ethyl ester is ring-closed with methylhydrazine to generate 3-(difluoromethyl)-1-methyl-1H-pyrazole-4-carboxylic acid ethyl ester (DFMMP), and the 3-(difluoromethyl)-1-methyl-1H-pyrazole-4-carboxylic acid ethyl ester (DFMMP) is hydrolyzed by sodium hydroxide and acidified with hydrochloric acid to obtain 3-(difluoromethyl)-1-methyl-1H-pyrazole-4-carboxylic acid (DFPA). Due to the high costs of this route, this method is generally no longer used in the researches on new synthesis methods except for the product lines that are already in production.

II. Method using dimethylaminoethyl acrylate, provided in patent WO2009043444 of Bayer, where similarly, in WO2009133178, BASF replaces dimethylamino with piperidinyl: In this method, a difluoroacetyl fluoride gas is introduced into ethyl dimethylaminoacrylate, an obtained intermediate is directly ring-closed with methylhydrazine to generate 3-(difluoromethyl)-1-methyl-1H-pyrazole-4-carboxylic acid ethyl ester (DFMMP), and the 3-(difluoromethyl)-1-methyl-1H-pyrazole-4-carboxylic acid ethyl ester (DFMMP) is hydrolyzed by sodium hydroxide and acidified with hydrochloric acid to obtain 3-(difluoromethyl)-1-methyl-1H-pyrazole-4-carboxylic acid (DFPA). The difluoroacetyl fluoride gas is obtained through pyrolysis of tetrafluoroethyl ether. This route is ingeniously designed, has features of short steps and a high yield, and is a method having relatively low costs at present. Disadvantages lie that this method has relatively high requirements for equipment, in addition, reactions may generate a large amount of volatile dimethylamine, which affects the environment, and further, the problem of selectivity of ring-closing with methylhydrazine to synthesize a pyrazole ring is not resolved.

III. Method using difluorochloroacetyl chloride, provided in the patent WO2012025469 of Solvay: This route was developed by Solvay, where difluorochloroacetyl chloride (CDFAC) is used as a starting material, reacts with ketene, and then, is quenched with ethanol, to obtain ethyl difluorochloroacetoacetate, so as to obtain 3-(difluorochloromethyl)-1-methyl-1H-pyrazole-4-carboxylic acid ethyl ester by using a method similar to the Claisen condensation method, the 3-(difluorochloromethyl)-1-methyl-1H-pyrazole-4-carboxylic acid ethyl ester is reduced with zinc powder or hydrogenated by palladium on carbon, to obtain 3-(difluoromethyl)-1-methyl-1H-pyrazole-4-carboxylic acid ethyl ester (DFMMP), and the 3-(difluoromethyl)-1-methyl-1H-pyrazole-4-carboxylic acid ethyl ester (DFMMP) is hydrolyzed by sodium hydroxide and acidified with hydrochloric acid to obtain 3-(difluoromethyl)-1-methyl-1H-pyrazole-4-carboxylic acid (DFPA). Disadvantage of this route lie in the relatively long route, the problem of sources of raw materials, and the problem of final dechlorination, which not only increases the costs, but also increases the three wastes.

IV. Other synthesis methods: 1) EP2008996 reports synthesizing 3-(difluoromethyl)-1-methyl-1H-pyrazole-4-carboxylic acid using raw materials, such as dichloroacetyl chloride, a vinyl ether compound, and methylhydrazine, in a 5-step reaction. Although this method has a specific advantage in control of costs, reaction conditions of this method are relatively harsh, where dichloroacetyl chloride and a vinyl ether compound need to react under the condition of −40 to −20° C. In a reaction of catalytically introducing a carboxyl group at an elevated pressure, the reaction temperature is 150° C., and the pressure in a kettle needs be constantly changed in this process, resulting in inconvenient operations and difficulty in separation of isomers. 2) WO2009000442 reports using ethyl difluoroacetate as a raw material to react with hydrazine hydrate to generate hydrazide, which after being methylated, is further ring-closed with ethyl propiolate to obtain 3-(difluoromethyl)-1-methyl-1H-pyrazole-4-carboxylic acid ethyl ester (DFMMP). The yield of this method is not high, and the price of ethyl propiolate is relatively high.

This method is not suitable for industrial production.

SUMMARY

A technical problem to be resolved by the present invention is to provide a halogen-substituted compound suitable for industrial production of a pyrazole derivative, a preparation method for the halogen-substituted compound, a preparation method for preparing a pyrazole derivative by using the halogen-substituted compound as an intermediate, and use of the halogen-substituted compound as an intermediate.

To resolve the foregoing technical problems, the present invention provides a technical solution: a preparation method for a halogen-substituted compound, where a piperazine derivative shown in formula I reacts with a halogenated acetyl halide derivative shown in formula VI to generate a halogen-substituted compound shown in formula II, where a reaction solvent is preferably chloroform, a catalyst is preferably triethylamine, and a reaction equation is as follows:

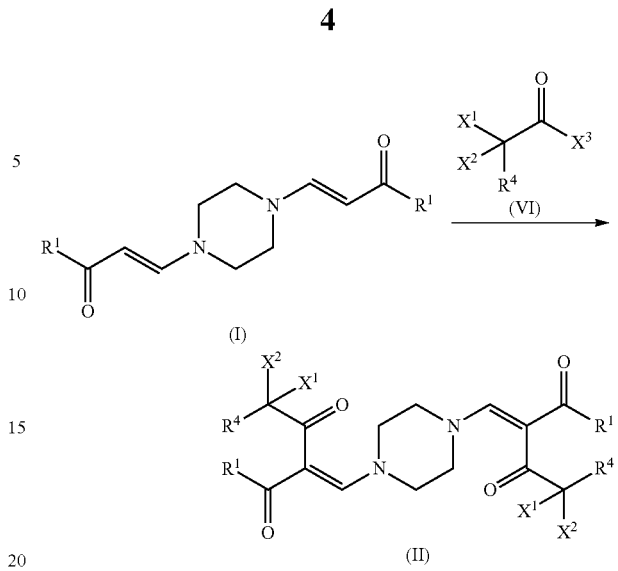

where:

$R^1$ is $OR^A$ or $R^A$, where $R^A$ is C1-C8 alkyl, C3-C8 cycloalkyl, C3-8 cycloalkyl with a substituent, aryl, aryl with a substituent, heteroaryl, or heteroaryl with a substituent;

$R^4$ is hydrogen, chlorine, fluorine, or C1-C8 alkyl; and $X^1$, $X^2$, and $X^3$ are each independently chlorine or fluorine.

Preferably, $X^1$, $X^2$, and $X^3$ are fluorine, $R^4$ is hydrogen, and $R^1$ is $OC_2H_5$ or $CH_3$.

To resolve the foregoing technical problems, the present invention provides a technical solution: a halogen-substituted compound, having a structure shown in formula II:

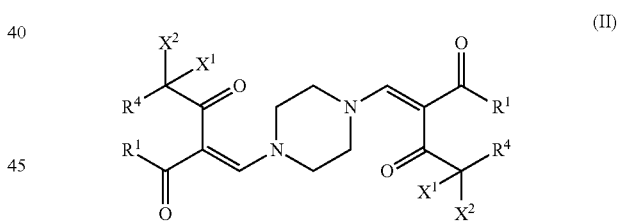

where:

$R^1$ is $OR^A$ or $R^A$, where $R^A$ is C1-C8 alkyl, C3-C8 cycloalkyl, C3-8 cycloalkyl with a substituent, aryl, aryl with a substituent, heteroaryl, or heteroaryl with a substituent;

$R^4$ is hydrogen, chlorine, fluorine, or C1-C8 alkyl; and $X^1$ and $X^2$ are each independently chlorine or fluorine.

Preferably, $X^1$ and $X^2$ are fluorine, $R^4$ is hydrogen, and R is $OC_2H$ or $CH_3$.

To resolve the foregoing technical problems, the present invention provides a technical solution: a preparation method for preparing a pyrazole derivative by using a halogen-substituted compound, where a halogen-substituted compound shown in formula II reacts with methylhydrazine to close a pyrazole ring, to generate a halogen-substituted alkyl-1-methylpyrazole derivative shown in formula IV, where a reaction equation is as follows:

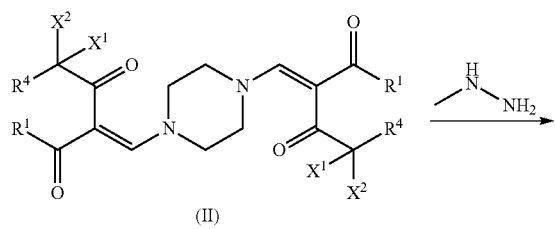

(II)

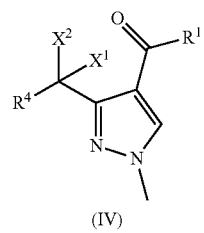

(IV)

where:

R¹ is OR$^A$ or R$^A$, where R$^A$ is C1-C8 alkyl, C3-C8 cycloalkyl, C3-8 cycloalkyl with a substituent, aryl, aryl with a substituent, heteroaryl, or heteroaryl with a substituent;

R⁴ is hydrogen, chlorine, fluorine, or C1-C8 alkyl; and

X¹ and X² are each independently chlorine or fluorine.

Preferably, X¹ and X² are fluorine, R⁴ is hydrogen, and R¹ is OC₂H₅ or CH₃.

When R¹ is OR$^A$, the halogen-substituted alkyl-1-methylpyrazole derivative shown in formula IV undergoes a hydrolysis reaction with an alkaline solution, where the alkaline solution is preferably a hydrogen sodium oxide solution, to generate halogen-substituted alkyl-1-methyl-1H-pyrazole-4-carboxylic acid shown in formula V. When R¹ is R$^A$, the halogen-substituted alkyl-1-methylpyrazole derivative shown in formula IV undergoes an oxidation reaction with an oxidant, where the oxidant is preferably a sodium hypochlorite solution, a sodium hypobromite solution, or oxygen, to generate halogen-substituted alkyl-1-methyl-1H-pyrazole-4-carboxylic acid shown in formula V, where a reaction equation is as follows:

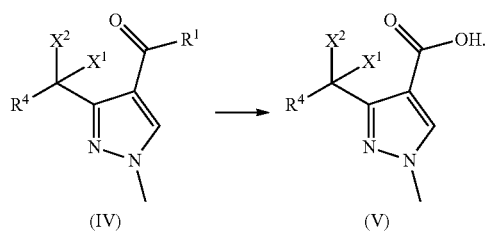

(IV) (V)

To resolve the foregoing technical problems, the present invention provides a technical solution: a preparation method for preparing a pyrazole derivative by using a halogen-substituted compound, where a halogen-substituted compound shown in formula II reacts with methylhydrazine benzaldehyde hydrazone to generate a hydrazone compound shown in formula III, where a reaction equation is as follows:

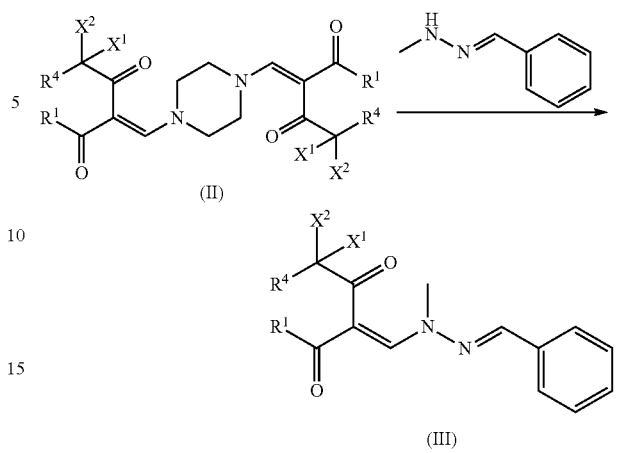

where:

R¹ is OR$^A$ or R$^A$, where R$^A$ is C1-C8 alkyl, C3-C8 cycloalkyl, C3-8 cycloalkyl with a substituent, aryl, aryl with a substituent, heteroaryl, or heteroaryl with a substituent;

R⁴ is hydrogen, chlorine, fluorine, or C1-C8 alkyl; and

X¹ and X² are each independently chlorine or fluorine.

Preferably, X¹ and X² are fluorine, R⁴ is hydrogen, and R¹ is OC₂H₅ or CH₃.

The hydrazone compound shown in formula III closes, under the action of an acid, where the acid is preferably sulfuric acid, a pyrazole ring to generate a halogen-substituted alkyl-1-methylpyrazole derivative shown in formula IV, where a reaction equation is as follows:

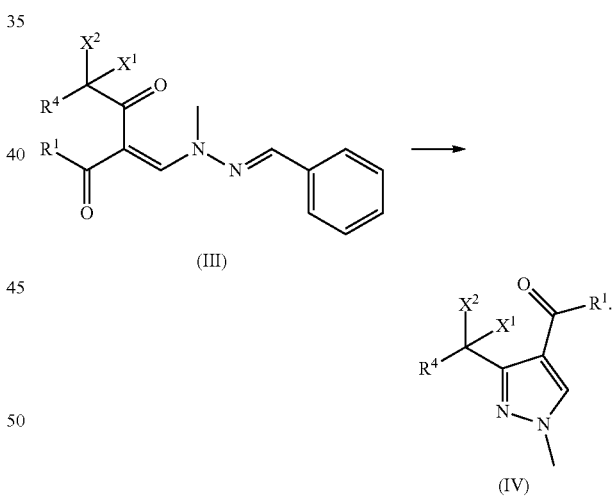

When R¹ is OR$^A$, the halogen-substituted alkyl-1-methylpyrazole derivative shown in formula IV undergoes a hydrolysis reaction with an alkaline solution, where the alkaline solution is preferably a hydrogen sodium oxide solution, to generate halogen-substituted alkyl-1-methyl-1H-pyrazole-4-carboxylic acid shown in formula V. When R¹ is R$^A$, the halogen-substituted alkyl-1-methylpyrazole derivative shown in formula IV undergoes an oxidation reaction with an oxidant, where the oxidant is preferably a sodium hypochlorite solution, a sodium hypobromite solution, or oxygen, to generate halogen-substituted alkyl-1-methyl-1H-pyrazole-4-carboxylic acid shown in formula V, where a reaction equation is as follows:

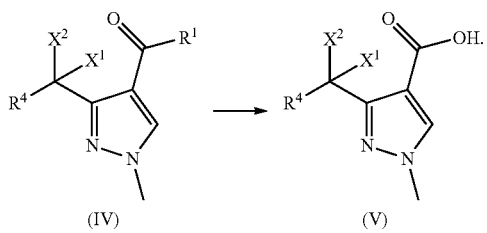

To resolve the foregoing technical problems, the present invention provides a technical solution: a method for preparing a pesticide, including the foregoing method for preparing a halogen-substituted compound or a pyrazole derivative. The pesticide is an amide fungicide, preferably Bixafen, Fluxapyroxad, Isopyrazam, or Sedaxane. The method for preparing a pesticide includes: converting halogen-substituted alkyl-1-methyl-1H-pyrazole-4-carboxylic acid into activated halogen-substituted alkyl-1-methyl-1H-pyrazole-4-carboxylic acid, preferably, by using a carboxylic acid halide, and then making the activated halogen-substituted alkyl-1-methyl-1H-pyrazole-4-carboxylic acid react with an amine, preferably aniline, to obtain an amide fungicide. For a specific preparation method, refer to the international patent WO1992/12970.

To resolve the foregoing technical problems, the present invention provides a technical solution: use of halogen-substituted alkyl-1-methyl-1H-pyrazole-4-carboxylic acid prepared by using the foregoing preparation method as an intermediate for preparing a pesticide. The pesticide is an amide fungicide, preferably Bixafen, Fluxapyroxad, Isopyrazam, or Sedaxane.

The present invention has the following advantageous effects:

(1) The present invention optimizes the structure of the halogen-substituted compound. Two N's of the halogen-substituted compound form piperazine, so that the halogen-substituted compound obtains a centrally symmetric structure. When the halogen-substituted compound of this structure is used to synthesize a pyrazole derivative, there are few reaction by-products. The reaction route of the present invention is short, the reaction conditions are common, where only a 40% aqueous alkylhydrazine compound solution is used, the yield of the reaction in each step is high, the intermediate is easy to purify, and the product has high quality. Compared with the structure of 3-piperidine cycloacrylate, the structure of the symmetric diamine has higher atom economy, and in addition, the symmetric diamine has a higher boiling point and is easier to recycle.

(2) The raw material compounds and the halogenated acetyl halide derivative used in the preparation of the halogen-substituted compound in the present invention are easy to prepare, can be directly outsourced, and have low raw material costs.

(3) In the present invention, when the pyrazole derivative is prepared, the halogen-substituted compound may first be used to react with methylhydrazine benzaldehyde hydrazone, and then, close a pyrazole ring under the action of an acid, where an advantage lies in that methylhydrazine benzaldehyde hydrazone forms a hydrazone protecting group, where the reaction can be carried out in the same reaction vessel, to further ensure that a ring-closed product without an isomer is obtained.

DETAILED DESCRIPTION OF THE EMBODIMENTS

The present invention is specifically described below by using examples. It should be noted that the following examples are merely used to further illustrate the present invention, and should not be understood as limitations on the scope of protection of the present invention. A person skilled in the art can make some non-essential improvements and adjustments to the present invention based on the foregoing content of the present invention.

Unless otherwise defined, all professional and scientific terms used in this application have the same meaning as those familiar to a person skilled in the art. For example, C1-C8 alkyl refers to alkyl having a carbon chain length of 1-8, for example, methyl, ethyl, propyl, isopropyl, butyl, isobutyl, sec-butyl, tert-butyl, amyl, hexyl, heptyl, or octyl. C3-C8 cycloalkyl refers to cycloalkyl having a carbon chain length of 3-8, for example, cyclopropyl, cyclobutyl, cyclopentyl, cyclohexyl, or cyclooctyl. C3-C8 cycloalkyl with a substituent is, for example, 2-methylcyclopropyl, 1-methylcyclopentyl, or 4-methylcyclohexyl. Aryl refers to a monovalent aromatic hydrocarbon group having a carbon chain length of 6-18, for example, phenyl, naphthyl, or anthracenyl. Aryl with a substituent is, for example, 3-methylphenyl (m-tolyl), 2,4-di-tert-butylphenyl, or 4-chlorine phenyl. Heteroaryl is, for example, furyl, pyrrolyl, indolyl, carbazolyl, or imidazolyl. Heteroaryl with a substituent refers to a group formed by substituting one or more hydrogen atoms of a heteroaryl group with a substituent.

In the examples of the present invention, the halogenated acetyl halide derivative shown in formula VI being difluorine acetyl fluorine is used as an example:

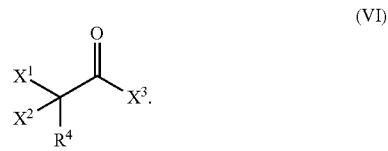

When $X^1$, $X^2$, and $X^3$ are fluorine, and $R^4$ is hydrogen, the halogenated acetyl halide derivative shown in formula VI is difluorine acetyl fluorine.

The difluorine acetyl fluorine gas can be formed through pyrolysis of tetrafluorine ether. The temperature of the pyrolysis reaction is 200° C. to 400° C., and the catalyst is aluminum oxide.

Example 1

Figure 1:
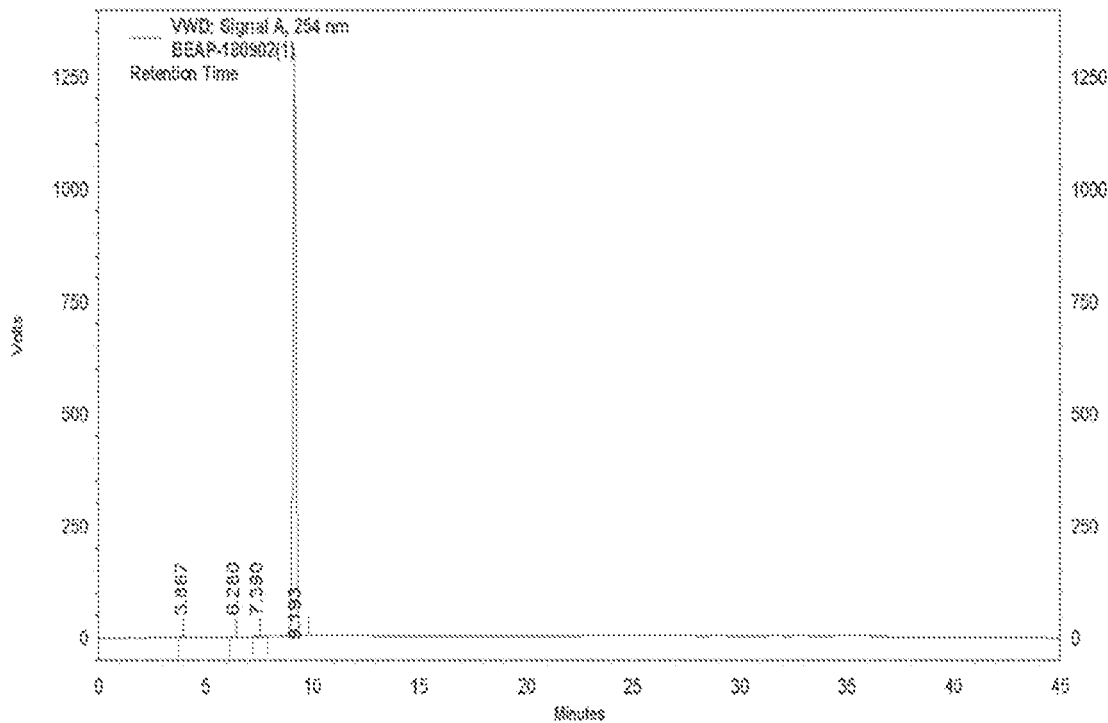
FIG. 1 is a high performance liquid chromatogram of N,N'-ethyl diacrylate piperazine in Example 1.
Figure 2:
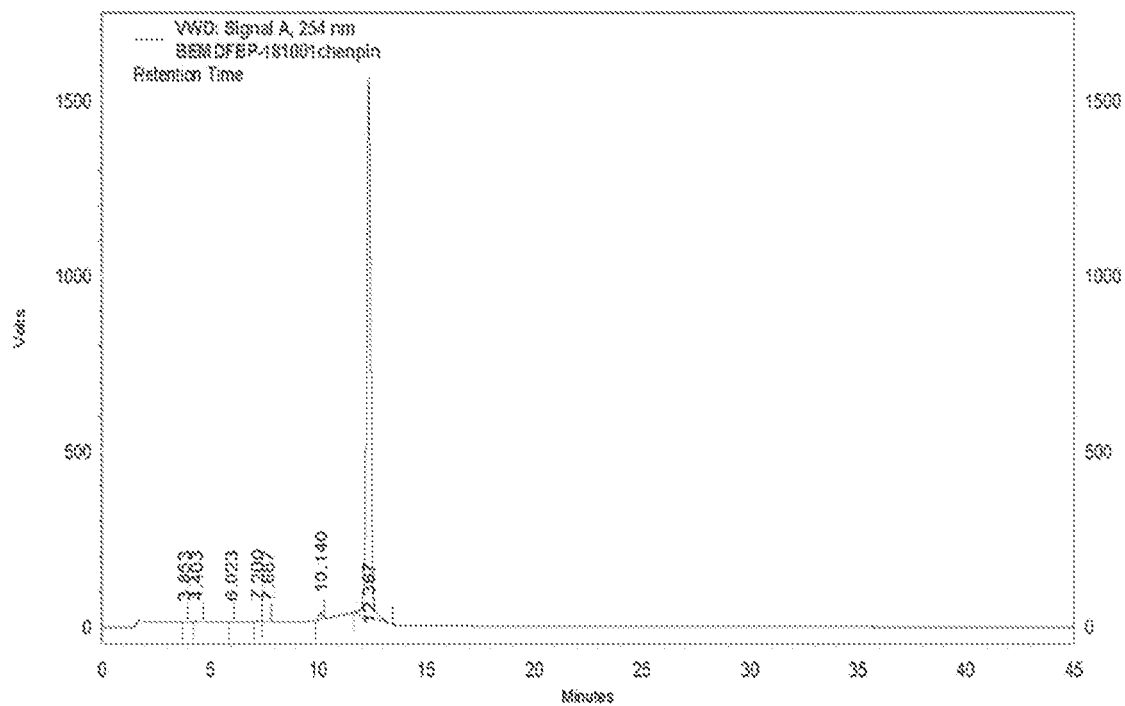
FIG. 2 is a high performance liquid chromatogram of a halogen-substituted compound in Example 1.
Figure 3:
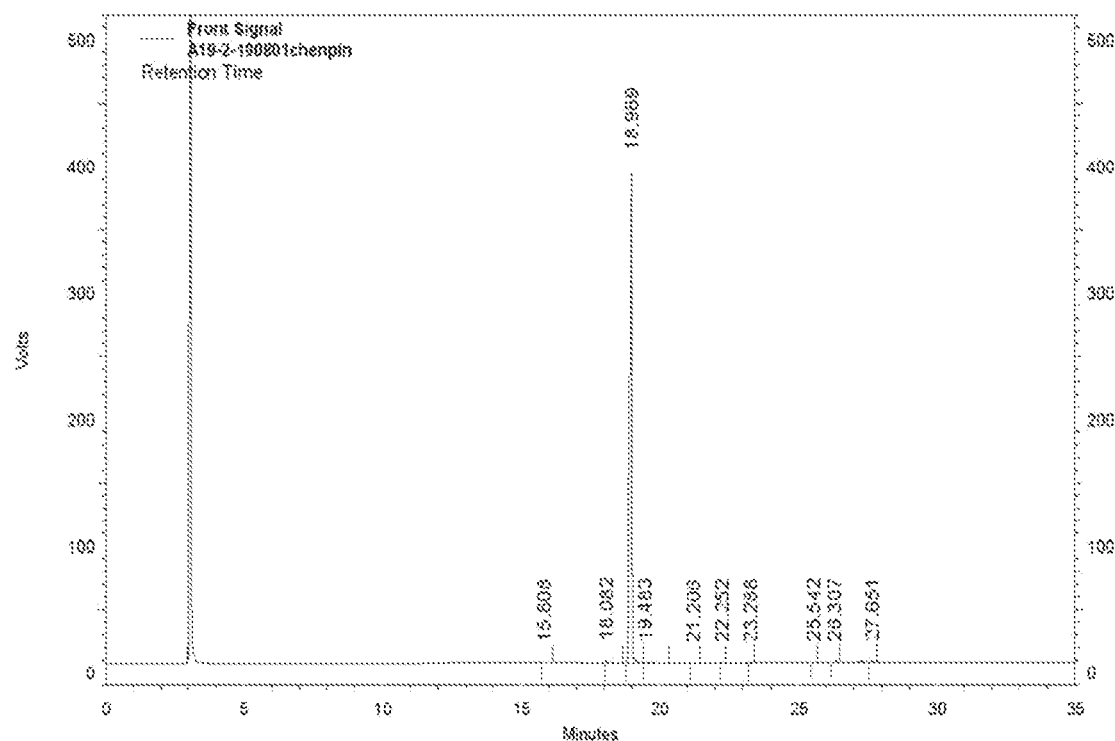
FIG. 3 is a gas chromatogram of 3-fluoroalkyl-1-methylpyrazole-4-carboxylic acid ethyl ester in Example 1.

A preparation method for a pyrazole derivative of this embodiment included the following steps:

28.2 g (0.1 mol) of N,N'-ethyl diacrylate piperazine (shown in formula I, where $R^1$ was $OC_2H_5$, and a high performance liquid chromatogram was shown in FIG. 1), 200 g of chloroform, and 22.2 g (0.22 mol) of triethylamine were added into a reaction flask, the temperature was controlled within 10° C. to 30° C., 21.5 g (0.22 mol) of difluorine acetyl fluorine (DFAF) was introduced, after the introduction of the gas was finished, the temperature was kept for reacting for 5 hours, a solvent was concentrated at a reduced pressure, 100 g of water was added into the residue, and the mixture was stirred for 30 minutes, and was filtered and dried to obtain 42.9 g of a corresponding halogen-substituted compound (shown in formula II, where a high performance liquid chromatogram was shown in FIG. 2), where the yield was 98%. 39 g (0.0889 mol) of the halogen-substituted compound product was suspended in 200 g of chloroform, the mixture was stirred and cooled to −25° C., 20.5 g (0.178 mol) of methylhydrazine (MMH) of which a concentration was 40% was added dropwise, after the addition was finished, the temperature was kept for reacting for 30 minutes and then, was raised to room temperature, a water layer was separated and removed, an organic layer was concentrated to dryness, and the residue was recrystallized by adding petroleum ether, to obtain 30.8 g of 3-fluoroalkyl-1-methylpyrazole-4-carboxylic acid ethyl ester (EDFMPA) (shown in formula IV), where the yield was 85%, and a gas chromatogram was shown in FIG. 3.

Figure 4:
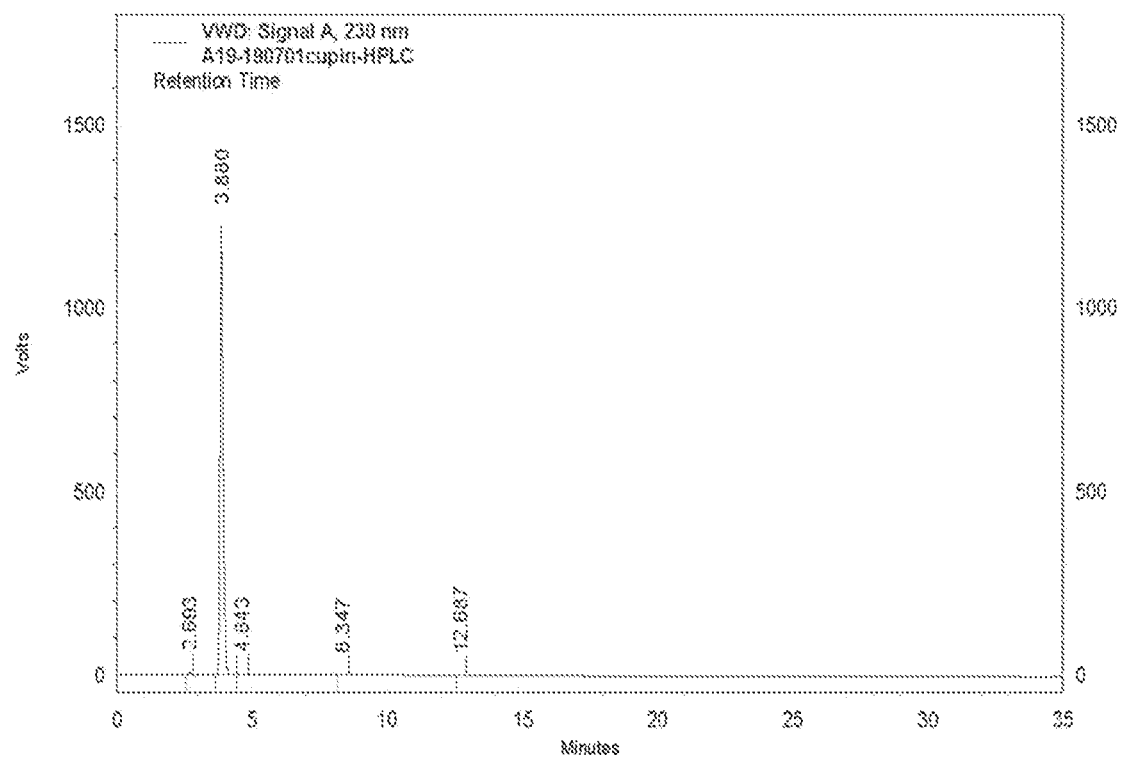
FIG. 4 is a high performance liquid chromatogram of 3-fluoroalkyl-1-methyl-1H-pyrazole-4-carboxylic acid in Example 1.

30.8 g (0.151 mol) of 3-fluoroalkyl-1-methylpyrazole-4-carboxylic acid ethyl ester (EDFMPA) was added into the reaction flask, 100 g of water and 6.7 g of hydrogen sodium oxide were added, the mixture was stirred for reacting for 2 hours at 70° C., after the reaction was finished, hydrochloric acid was added dropwise to neutralize the product to a pH value of 2, the product was cooled to 10° C., filtered, washed with a small amount of cold water, and dried, to obtain 25.2 g of 3-fluoroalkyl-1-methyl-1H-pyrazole-4-carboxylic acid (DFMPA) (shown in formula V), where the yield was 95%, the purity detected through high performance liquid chromatography was 99%, and a high performance liquid chromatogram was shown in FIG. 4.

Example 2

A preparation method for a pyrazole derivative of this embodiment included the following steps:

28.2 g (0.1 mol) of N,N'-ethyl diacrylate piperazine (shown in formula I, where $R^1$ was $OC_2H_5$), 200 g of chloroform, and 22.2 g (0.22 mol) of triethylamine were added into a reaction flask, the temperature was controlled within 10° C. to 30° C., 21.5 g (0.22 mol) of difluorine acetyl fluorine (DFAF) was introduced, after the introduction of the gas was finished, the temperature was kept for reacting for 5 hours, after the reaction was finished, 26.8 g (0.2 mol) of methylhydrazine benzaldehyde hydrazone (BzH) was added dropwise, the temperature was raised to 50° C. and was kept for reacting for 3 hours, a solvent was evaporated at a reduced pressure, 200 g of chloroform and 5 g of sulfuric acid were further added to the residue for reacting at room temperature for 8 hours, 50 g of water was added, an organic layer was separated and heated to 60° C., and 90 g of a sodium hydroxide solution of which a concentration was 10% was added dropwise. After the addition was finished, the reaction continued for 3 hours, after the reaction was finished, a water layer was separated, hydrochloric acid was added dropwise to neutralize the product to a pH value of 2, and the product was cooled to 10° C., filtered, washed with water, and dried, to obtain 26 g of 3-fluoroalkyl-1-methyl-1H-pyrazole-4-carboxylic acid (DFMPA) (shown in formula V), where the total yield was 73.8%, and the purity detected through high performance liquid chromatography was 99%.

Example 3

A preparation method for a pyrazole derivative of this embodiment included the following steps:

22.2 g (0.1 mol) of N,N'-divinylmethylketopiperazine (shown in formula I, where $R^1$ was $CH_3$), 200 g of chloroform, and 22.2 g (0.22 mol) of triethylamine were added into a reaction flask, the temperature was controlled within 10° C. to 30° C., 21.5 g (0.22 mol) of difluorine acetyl fluorine (DFAF) was introduced, after the introduction of the gas was finished, the temperature was kept for reacting for 5 hours, 26.8 g (0.2 mol) of methylhydrazine benzaldehyde hydrazone (BzH) was added dropwise, the temperature was raised to 50° C. and was kept for reacting for 3 hours, a solvent was evaporated at a reduced pressure, 200 g of chloroform and 5 g of sulfuric acid were further added to the residue for reacting at room temperature for 8 hours, 50 g of water was added, an organic layer was separated and concentrated to dryness, was recrystallized by adding petroleum ether, and was filtered and dried to obtain 27.2 g of a 3-trifluoromethyl-1-methyl-4-acetylpyrazole derivative (shown in formula IV), where the yield was 78%.

25 g (0.14 mol) of the 3-trifluoromethyl-1-methyl-4-acetylpyrazole derivative, 80 g of acetic acid, 1 g of manganese nitrate, and 1 g of ferric nitrate were added into the reaction flask, the temperature was raised to 80° C., oxygen was introduced for reacting for 20 hours, the acetic acid was evaporated at a reduced pressure, 80 g of water was added to the residue, the mixture was stirred, heated to 80° C., cooled to 10° C., filtered, and dried to obtain 24 g of 3-fluoroalkyl-1-methyl-1H-pyrazole-4-carboxylic acid (DFMPA) (as shown in formula V), where the yield was 95%, and the purity detected through high performance liquid chromatography was 99%.

Obviously, the foregoing examples are merely examples provided for clearly illustrating the present invention, and are not intended to limit the implementations of the present invention. A person of ordinary skill in the art may alternatively make other changes or modifications in different forms based on the foregoing description. It is unnecessary and impossible to exhaustively list all the implementations in this application. Moreover, the obvious changes or modifications derived from the spirit of the present invention still fall within the scope of protection of the present invention.

What is claimed is:

1. A halogen-substituted compound, having a structure shown in formula II:

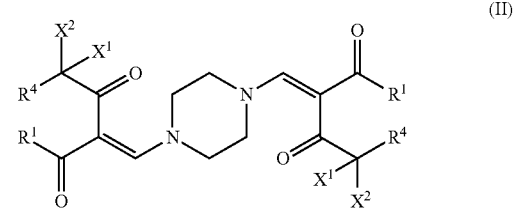

wherein:
$R^1$ is $OR^4$ or $R^4$, wherein $R^4$ is C1-C8 alkyl, C3-C8 cycloalkyl, aryl, heteroaryl, 2-methylcyclopropyl, 1-methycyclopentyl, 4-methylcyclohexyl, 3-methylphenyl(m-tolyl), 2,4-di-tert-butylphenyl, or 4-chlorophenyl;
$R^4$ is hydrogen, chlorine, fluorine, or C1-C8 alkyl; and
$X^1$ and $X^2$ are each independently chlorine or fluorine.

2. A preparation method for the halogen-substituted compound according to claim 1, wherein:
a piperazine derivative shown in formula I reacts with a halogenated acetyl halide derivative shown in formula VI to generate the halogen-substituted compound shown in formula II, wherein a reaction equation is as follows:

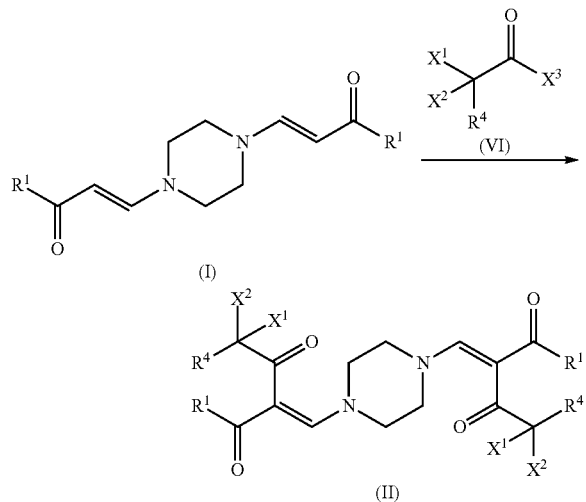

wherein:
$R^1$ is $OR^A$ or $R^A$, wherein $R^A$ is C1-C8 alkyl, C3-C8 cycloalkyl, aryl, heteroaryl, 2-methylcyclopropyl, 1-methycyclopentyl, 4-methylcyclohexyl, 3-methylphenyl(m-tolyl), 2,4-di-tert-butylphenyl, or 4-chlorophenyl;
$R^4$ is hydrogen, chlorine, fluorine, or C1-C8 alkyl; and
$X^1$, $X^2$, and $X^3$ are each independently chlorine or fluorine.

3. A preparation method for preparing a halogen-substituted alkyl-1-methyl pyrazole of formula IV, wherein:
the halogen-substituted compound shown in formula II reacts with methylhydrazine to close a pyrazole ring, to generate a halogen-substituted alkyl-1-methylpyrazole shown in formula IV, wherein a reaction equation is as follows:

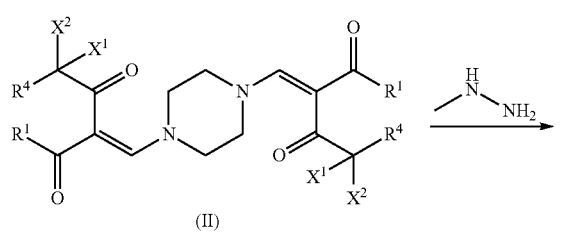

wherein:
$R^1$ is $OR^A$ or $R^A$, wherein $R^A$ is C1-C8 alkyl, C3-C8 cycloalkyl, aryl, heteroaryl, 2-methylcyclopropyl, 1-methycyclopentyl, 4-methylcyclohexyl, 3-methylphenyl(m-tolyl), 2,4-di-tert-butylphenyl, or 4-chlorophenyl;
$R^4$ is hydrogen, chlorine, fluorine, or C1-C8 alkyl; and
$X^1$ and $X^2$ are each independently chlorine or fluorine.

4. The preparation method according to claim 3, wherein when $R^1$ is $OR^A$, the halogen-substituted alkyl-1-methylpyrazole shown in formula IV undergoes a hydrolysis reaction to generate a halogen-substituted alkyl-1-methyl-1H-pyrazole-4-carboxylic acid shown in formula V, wherein a reaction equation of the hydrolysis reaction is as follows:

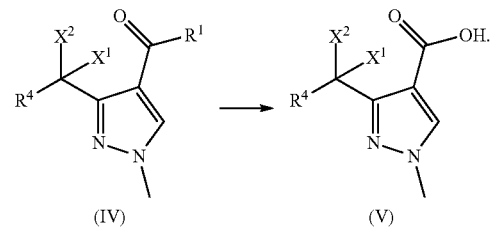

5. The preparation method according to claim 3, wherein when $R^1$ is $R^A$, the halogen-substituted alkyl-1-methylpyrazole shown in formula IV undergoes an oxidation reaction to generate a halogen-substituted alkyl-1-methyl-1H-pyrazole-4-carboxylic acid shown in formula V, wherein a reaction equation of the oxidation reaction is as follows:

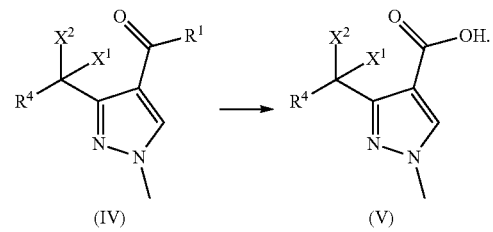

6. A preparation method for preparing a halogen-substituted alkyl-1-methyl pyrazole of formula IV, wherein:
the halogen-substituted compound shown in formula II reacts with methylhydrazine benzaldehyde hydrazone to generate a hydrazone compound shown in formula III, wherein a reaction equation is as follows:

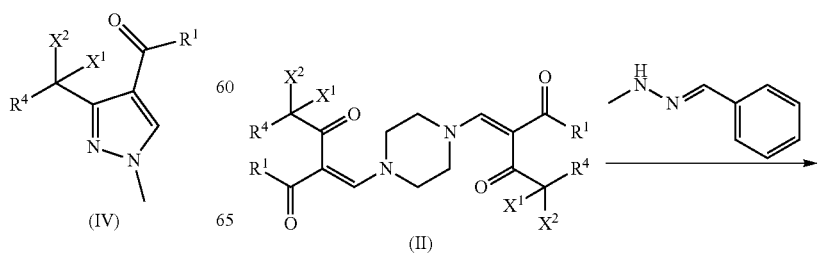

-continued

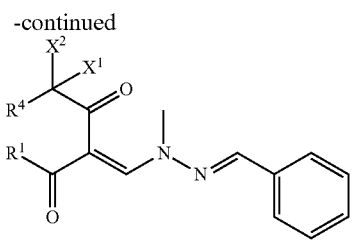

(III)

wherein:
R¹ is OR^A or R^A, wherein R^A is C1-C8 alkyl, C3-C8 cycloalkyl, aryl, heteroaryl, 2-methylcyclopropyl, 1-methycyclopentyl, 4-methylcyclohexyl, 3-methylphenyl(m-tolyl), 2,4-di-tert-butylphenyl, or 4-chlorophenyl;
R⁴ is hydrogen, chlorine, fluorine, or C1-C8 alkyl; and
X¹ and X² are each independently chlorine or fluorine; and
the hydrazone compound shown in formula III closes, under the action of an acid, a pyrazole ring to generate a halogen-substituted alkyl-1-methylpyrazole shown in formula IV, wherein a reaction equation is as follows:

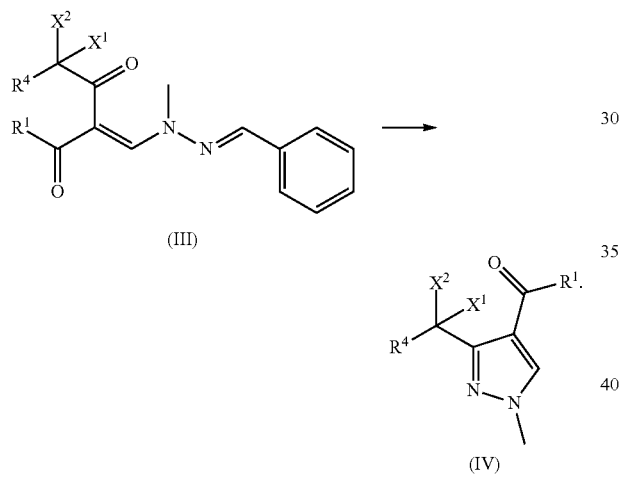

7. The preparation method according to claim 6, wherein when R¹ is OR^A, the halogen-substituted alkyl-1-methylpyrazole shown in formula IV undergoes a hydrolysis reaction to generate a halogen-substituted alkyl-1-methyl-1H-pyrazole-4-carboxylic acid shown in formula V, wherein a reaction equation of the hydrolysis reaction is as follows:

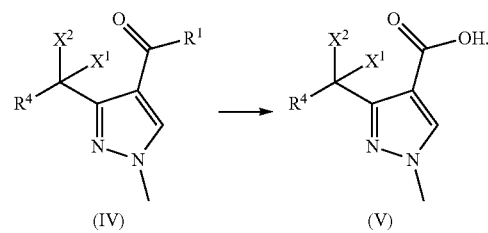

8. The preparation method according to claim 6, wherein when R¹ is R^A, the halogen-substituted alkyl-1-methylpyrazole shown in formula IV undergoes an oxidation reaction to generate a halogen-substituted alkyl-1-methyl-1H-pyrazole-4-carboxylic acid shown in formula V, wherein a reaction equation of the oxidation reaction is as follows:

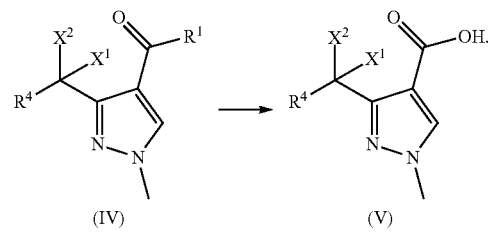

* * * * *